(12) United States Patent
Palushi et al.

(10) Patent No.: US 10,835,327 B2
(45) Date of Patent: Nov. 17, 2020

(54) SENSOR GUIDED INSTRUMENT WITH PENETRATING FEATURE

(71) Applicant: Acclarent, Inc., Irvine, CA (US)

(72) Inventors: Jetmir Palushi, Irvine, CA (US); Paul D. DeCosta, Livermore, CA (US)

(73) Assignee: Acclarent, Inc., Irvine, CA (US)

(*) Notice: Subject to any disclaimer, the term of this patent is extended or adjusted under 35 U.S.C. 154(b) by 282 days.

(21) Appl. No.: 15/695,520

(22) Filed: Sep. 5, 2017

(65) Prior Publication Data
US 2019/0069959 A1 Mar. 7, 2019

(51) Int. Cl.
*A61B 34/30* (2016.01)
*A61B 10/02* (2006.01)
(Continued)

(52) U.S. Cl.
CPC ............... *A61B 34/30* (2016.02); *A61B 5/06* (2013.01); *A61B 5/062* (2013.01); *A61B 5/150198* (2013.01); *A61B 10/0233* (2013.01); *A61B 10/0283* (2013.01); *A61B 10/04* (2013.01); *A61B 17/24* (2013.01); *A61B 17/3403* (2013.01); *A61B 17/3478* (2013.01); *A61B 34/20* (2016.02); *A61B 90/14* (2016.02); *A61M 5/3287* (2013.01); *A61B 34/25* (2016.02); *A61B 2010/045* (2013.01); *A61B 2034/105* (2016.02); *A61B 2034/2051* (2016.02); *A61B 2034/2065* (2016.02); *A61B 2034/2072* (2016.02);
(Continued)

(58) Field of Classification Search
CPC ........................................................ A61B 5/06
See application file for complete search history.

(56) References Cited

U.S. PATENT DOCUMENTS 6,961,608 B2 * 11/2005 Hoshino .............. G01R 33/287
128/899
7,720,521 B2  5/2010 Chang et al.
(Continued)

FOREIGN PATENT DOCUMENTS

WO  WO 2008/105874 A1   9/2008
WO  WO 2016/183226 A1   11/2016

OTHER PUBLICATIONS

Park et al. "Real-Time Estimation of 3-D Needle Shape and Deflection for MRI-Guided Interventions". IEEE ASME Trans Mechatron . Dec. 2010 ; 15(6): 906-915. doi:10.1109/TMECH. 2010.2080360. (Year: 2010).*

(Continued)

*Primary Examiner* — Amanda Lauritzen Moher
*Assistant Examiner* — Jillian K. McGough
(74) *Attorney, Agent, or Firm* — Frost Brown Todd LLC

(57) ABSTRACT

A surgical instrument includes a catheter, a distal segment, a needle, and a tracking sensor. The catheter is configured to be inserted into an anatomical passageway of a patient and includes a catheter lumen. The distal segment includes a port that communicates with the catheter lumen. The needle is slidably disposed within the catheter lumen and is translatable relative to the catheter between a retracted position and an extended position. A needle distal end is configured to extend through the port when the needle is in the extended position. The tracking sensor is coupled to the needle and is configured to generate a signal corresponding to a location of the needle distal end within the patient.

20 Claims, 6 Drawing Sheets

(51) Int. Cl.
  *A61M 5/32* (2006.01)
  *A61B 17/34* (2006.01)
  *A61B 5/15* (2006.01)
  *A61B 5/06* (2006.01)
  *A61B 17/24* (2006.01)
  *A61B 34/20* (2016.01)
  *A61B 10/04* (2006.01)
  *A61B 90/14* (2016.01)
  *A61B 90/00* (2016.01)
  *A61B 34/00* (2016.01)
  *A61B 34/10* (2016.01)

(52) U.S. Cl.
  CPC ... *A61B 2090/062* (2016.02); *A61B 2090/365* (2016.02); *A61B 2090/397* (2016.02)

(56) References Cited

U.S. PATENT DOCUMENTS

| | | | |
|---|---|---|---|
| 8,123,722 | B2 | 2/2012 | Chang et al. |
| 8,190,389 | B2 | 5/2012 | Kim et al. |
| 8,320,711 | B2 | 11/2012 | Altmann et al. |
| 8,632,468 | B2 | 1/2014 | Glossop et al. |
| 8,702,626 | B1 | 4/2014 | Kim et al. |
| 9,167,961 | B2 | 10/2015 | Makower et al. |
| 9,198,736 | B2 | 12/2015 | Kim et al. |
| 2004/0171934 | A1* | 9/2004 | Khan ............... A61B 5/06 600/435 |
| 2007/0208252 | A1 | 9/2007 | Makower |
| 2010/0030031 | A1 | 2/2010 | Goldfarb et al. |
| 2010/0076303 | A1* | 3/2010 | McKinley ......... A61B 17/3478 600/424 |
| 2010/0217117 | A1* | 8/2010 | Glossop ............. A61B 8/4245 600/424 |
| 2010/0317961 | A1* | 12/2010 | Jenkins ............... A61B 18/02 600/411 |
| 2011/0004057 | A1 | 1/2011 | Goldfarb et al. |
| 2011/0060214 | A1 | 3/2011 | Makower |
| 2013/0079628 | A1* | 3/2013 | Groszmann ........... A61B 6/12 600/424 |
| 2013/0317339 | A1 | 11/2013 | Waldstreicher et al. |
| 2014/0046261 | A1* | 2/2014 | Newman .......... A61M 25/0127 604/158 |
| 2014/0200444 | A1 | 7/2014 | Kim et al. |
| 2014/0364725 | A1 | 12/2014 | Makower |
| 2015/0305770 | A1* | 10/2015 | Fill ................. A61B 18/1477 600/424 |
| 2016/0008083 | A1 | 1/2016 | Kesten et al. |
| 2016/0310042 | A1 | 10/2016 | Kesten et al. |
| 2016/0331343 | A1* | 11/2016 | Hunter ............... A61B 8/445 |
| 2017/0043100 | A1* | 2/2017 | Nguyen ............ A61B 17/3415 |

OTHER PUBLICATIONS

International Search Report and Written Opinion dated Dec. 10, 2018 for Application No. PCT/IB2018/056391, 12 pgs.

* cited by examiner

SENSOR GUIDED INSTRUMENT WITH PENETRATING FEATURE

BACKGROUND

Sinusitis is the inflammation or infection of the paranasal sinuses, generally caused by bacteria, viruses, fungi (molds), allergies or combinations thereof. To facilitate proper diagnosis of a suspected case of sinusitis, a surgeon may collect one or more biopsy samples of the affected tissue with a biopsy instrument, such as a needle aspiration instrument, directed through the patient's nose and into the paranasal sinus. In some conventional settings, such biopsy procedures may be performed using functional endoscopic sinus surgery (FESS). In FESS, an endoscope is inserted into the nose and, under visualization through the endoscope, the surgeon collects the biopsy sample with the surgical instrument.

FESS procedures may be performed with a variable direction view endoscope that provides visualization within the paranasal sinuses or other anatomical passageway being accessed (e.g., of the ear, nose, or throat). A variable direction view endoscope may enable viewing along a variety of transverse viewing angles without having to flex the shaft of the endoscope within the anatomical passageway. Such an endoscope may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Irvine, Calif.

During an FESS procedure, the surgeon may also dilate the anatomical passageway being accessed. This may include dilation of ostia of paranasal sinuses (e.g., to treat sinusitis), dilation of the larynx, dilation of the Eustachian tube, or dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

In some instances, sinus and ENT surgery may be performed with the assistance of electronic navigation devices, referred to as image-guided surgery (IGS). IGS is a procedure in which a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

Examples of electromagnetic IGS systems that may be used in ENT and sinus surgery include the InstaTrak ENT™ systems available from GE Medical Systems, Salt Lake City, Utah. Other examples of electromagnetic image guidance systems include but are not limited to the CARTO® 3 System by Biosense-Webster, Inc., of Diamond Bar, Calif.; and systems available from Surgical Navigation Technologies, Inc., of Louisville, Colo. An example of an endobronchial instrument that may be used with an IGS system is described in U.S. Pub. No. 2013/0317339, entitled "Endobronchial Catheter," published Nov. 28, 2013, now abandoned, the disclosure of which is incorporated by reference herein.

When applied to functional endoscopic sinus surgery (FESS), sinus biopsy procedures, balloon sinuplasty, and/or other ENT procedures, the use of IGS allows the surgeon to achieve more precise movement and positioning of the surgical instruments than can be achieved by viewing through an endoscope alone. This is so because a typical endoscopic image is a spatially limited, 2-dimensional, line-of-sight view. The use of image guidance systems provides a real time, 3-dimensional view of all of the anatomy surrounding the operative field, not just that which is actually visible in the spatially limited, 2-dimensional, direct line-of-sight endoscopic view. As a result, image guidance systems may be particularly useful during performance of FESS, sinus biopsy procedures, balloon sinuplasty, and/or other ENT procedures, especially in cases where normal anatomical landmarks are not present or are difficult to visualize endoscopically.

While several systems and methods have been made and used in ENT procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
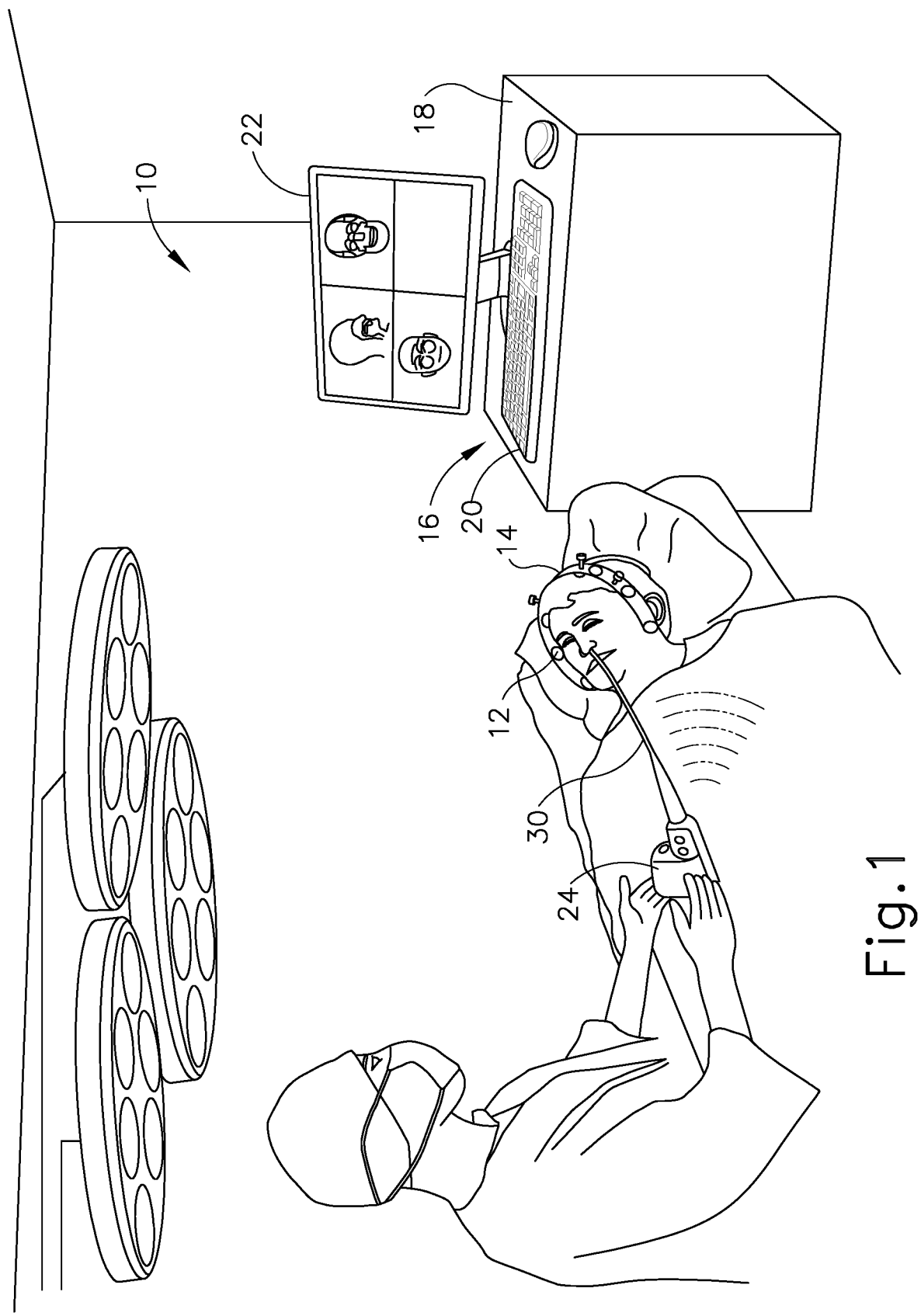
FIG. 1 depicts a schematic perspective view of an exemplary surgery navigation system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Image Guided Navigation System

A. Overview of Image Guided Navigation System

Figure 2:
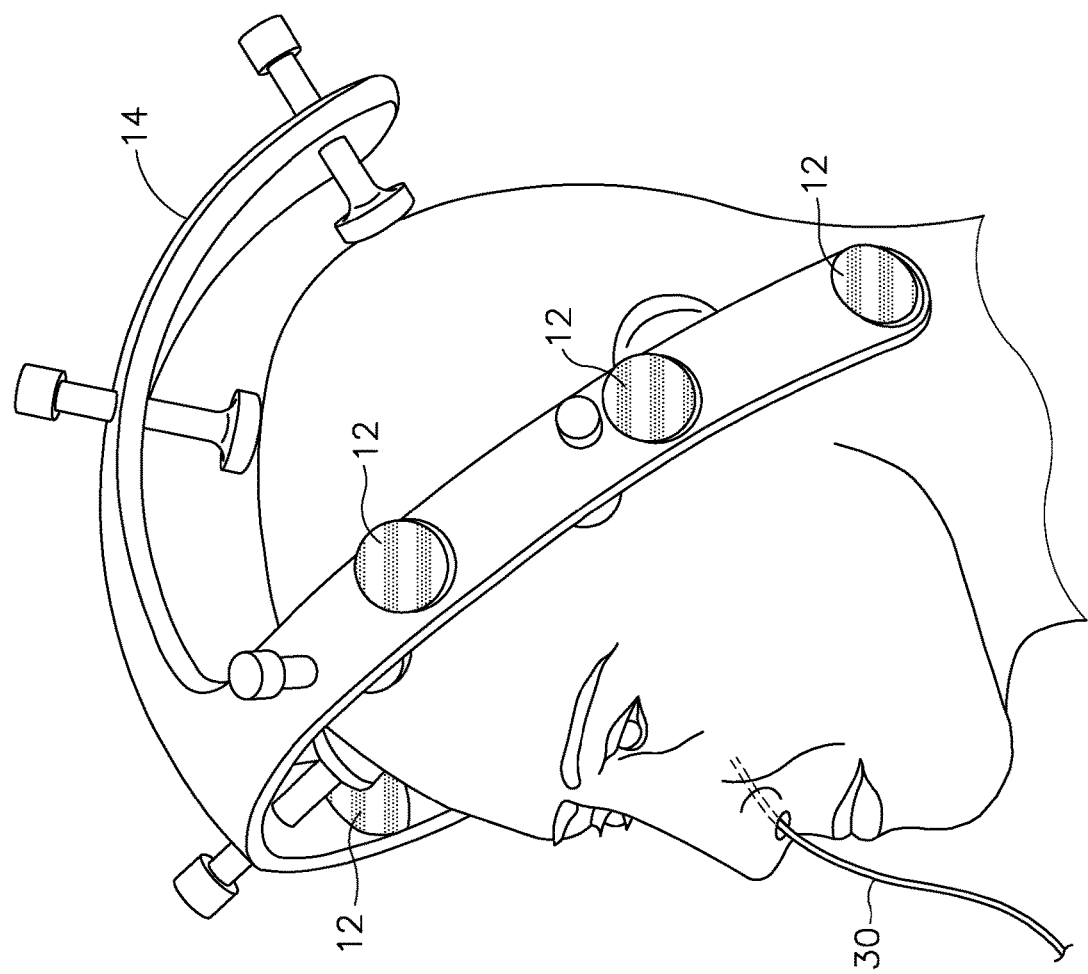
FIG. 2 depicts a perspective view of the head of a patient, with components of the surgery navigation system of FIG. 1.

FIGS. 1 and 2 show an exemplary image-guided surgery (IGS) navigation system (10) with which an ENT procedure may be performed using IGS. In particular, IGS navigation system (10) is implemented in combination with a sensor guided instrument (30) for collecting one or more biopsy samples and/or delivering a liquid substance such as a therapeutic drug or irrigation fluid to tissue at a selected surgical site. While IGS navigation system (10) is shown being employed for conducting a sinus surgical procedure, it will be understood that IGS navigation system (10) may be readily employed for conducting procedures in various other portions of the body, such as in the lungs and connecting passageways, for example.

IGS navigation system (10) of the present example includes a set of magnetic field generators (12). Before a surgical procedure begins, field generators (12) are fixed to the head of the patient. As best seen in FIG. 2, field generators (12) are incorporated into a frame (14), which is clamped to the head of the patient. While field generators (12) are secured to the head of the patient in this example, it should be understood that field generators (12) may instead be positioned at various other suitable locations and on various other suitable structures. By way of example only, field generators (12) may be mounted on an independent structure that is fixed to a table or chair on which the patient is positioned, on a floor-mounted stand that has been locked in position relative to the head of the patient, and/or at any other suitable location(s) and/or on any other suitable structure(s).

Field generators (12) are operable to generate an electromagnetic field around the head of the patient. In particular, field generators (12) are operated so as to transmit alternating magnetic fields of different frequencies into a region in proximity to frame (14). Various suitable components that may be used to form and drive field generators (12) will be apparent to those of ordinary skill in the art in view of the teachings herein. Field generators (12) enable tracking of the position of a distal end of sensor guided instrument (30) inserted into an anatomical passageway of the patient. In particular, as described in greater detail below, sensor guided instrument (30) includes one or more electromagnetic sensors, such as coils, mounted at a distal portion of instrument (12) and configured to interact with the electromagnetic field generated by field generators (12). Each electromagnetic sensor is configured to generate an electric signal in response to movement of the sensor through the electromagnetic field, and communicate the signal to a processor (16) of IGS navigation system (10). Processor (16) then processes the signals and determines the three-dimensional location of the distal portion of sensor guided instrument (30) within the patient.

Processor (16) of IGS navigation system (10) comprises a processing unit that communicates with one or more memories, and is configured to control field generators (12) and other elements of IGS navigation system (10). In the present example, processor (16) is mounted in a console (18), which comprises operating controls (20) that include a keypad and/or a pointing device such as a mouse or trackball. A physician uses operating controls (20) to interact with processor (16) while performing the surgical procedure. Processor (16) uses software stored in a memory of processor (16) to calibrate and operate system (10). Such operation includes driving field generators (12), processing data from sensor guided instrument (30), processing data from operating controls (20), and driving display screen (22). The software may be downloaded to processor (16) in electronic form, over a network, for example, or it may, alternatively or additionally, be provided and/or stored on non-transitory tangible media, such as magnetic, optical, or electronic memory.

Processor (16) is further operable to provide video in real time via display screen (22), showing the position of the distal portion of sensor guided instrument (30) in relation to a video camera image of the patient's head, a CT scan image of the patient's head, and/or a computer generated three-dimensional model of the anatomy within and adjacent to the patient's nasal cavity. Display screen (22) may display such images simultaneously and/or superimposed on each other. Moreover, display screen (22) may display such images during the surgical procedure. Such displayed images may also include graphical representations of instruments that are inserted in the patient's head, such as sensor guided instrument (30), such that the operator may view the virtual rendering of the instrument at its actual location in real time. Such graphical representations may actually look like the instrument or may be a much simpler representation such as a dot, crosshairs, etc. By way of example only, display screen (22) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (22). The images provided through display screen (22) may help guide the operator in maneuvering and otherwise manipulating instruments within the patient's head.

Any suitable device may be used to generate a three-dimensional model of the anatomy within and adjacent to the patient's nasal cavity before sensor guided instrument (30) is deployed into the patient's nasal cavity, or other body portion. By way of example only, a model of this anatomy may be generated in accordance with at least some of the teachings of U.S. Pub. No. 2016/0310042, entitled "System and Method to Map Structures of Nasal Cavity," published Oct. 27, 2016, issued as U.S. Pat. No. 10,362,965 on Jul. 30, 2019, the disclosure of which is incorporated by reference herein. Still other suitable ways in which a three-dimensional model of the anatomy within and adjacent to the patient's nasal cavity may be generated will be apparent to those of ordinary skill in the art in view of the teachings herein. It should also be understood that, regardless of how or where the three-dimensional model of the anatomy within and adjacent to the patient's nasal cavity is generated, the model may be stored on console (18). Console (18) may thus render images of at least a portion of the model via display screen (22) and further render real-time video images of the position of sensor guided instrument (30) in relation to the model via display screen (22).

In addition to connecting to processor (16) and operating controls (20), console (18) may also connect to other elements of system (10). For instance, as shown in FIG. 1, a coupling unit (24) may be secured to the proximal end of sensor guided instrument (30). Coupling unit (24) of this example is configured to provide wireless communication of data and other signals between console (18) and sensor guided instrument (30). In some versions, coupling unit (24) simply communicates data or other signals from sensor guided instrument (30) to console (18) uni-directionally, without also communicating data or other signals from console (18). In some other versions, coupling unit (24) provides bi-directional communication of data or other signals between sensor guided instrument (30) and console (18). While coupling unit (24) of the present example couples with console (18) wirelessly, some other versions may provide wired coupling between coupling unit (24) and console (18). Various other suitable features and functionality that may be incorporated into coupling unit (24) will be apparent to those of ordinary skill in the art in view of the teachings herein.

In addition to, or in lieu of, having the components and operability described herein, IGS navigation system (10) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Similarly, in addition to or in lieu of having the components and operability described herein, IGS navigation system (10) may be constructed and operable in accordance with at least some of the teachings of U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pat. Pub. No. 2014/0200444, entitled "Guidewires for Performing Image Guided Procedures," published Jul. 17, 2014, now abandoned, the disclosure of which is incorporated by reference herein; U.S. Pat. No. 9,198,736, entitled "Adapter for Attaching Electromagnetic Image Guidance Components to a Medical Device," issued Dec. 1, 2015, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein; U.S. Pat. No. 9,167,961, entitled "Methods and Apparatus for Treating Disorders of the Ear Nose and Throat," issued Oct. 27, 2015, the disclosure of which is incorporated by reference herein; and U.S. Pat. Pub. No. 2007/0208252, now abandoned, entitled "Systems and Methods for Performing Image Guided Procedures within the Ear, Nose, Throat and Paranasal Sinuses," published Sep. 6, 2007, the disclosure of which is incorporated by reference herein.

B. Exemplary Sensor Guided Instrument Having Needle Mounted Sensor Coil

Figure 3:
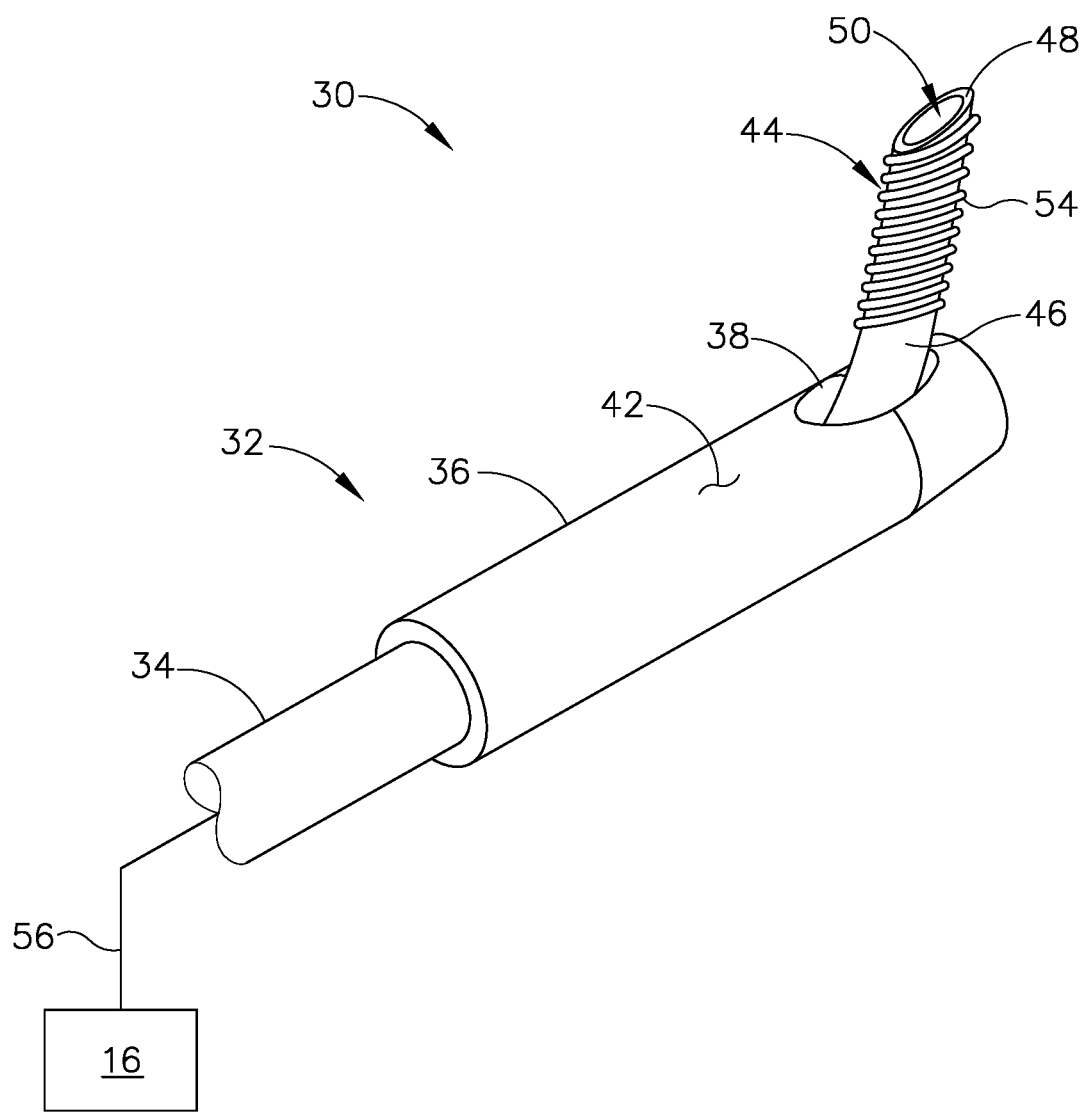
FIG. 3 depicts a perspective view of an exemplary sensor guided instrument of the surgery navigation system of FIG. 1.
Figure 4A:
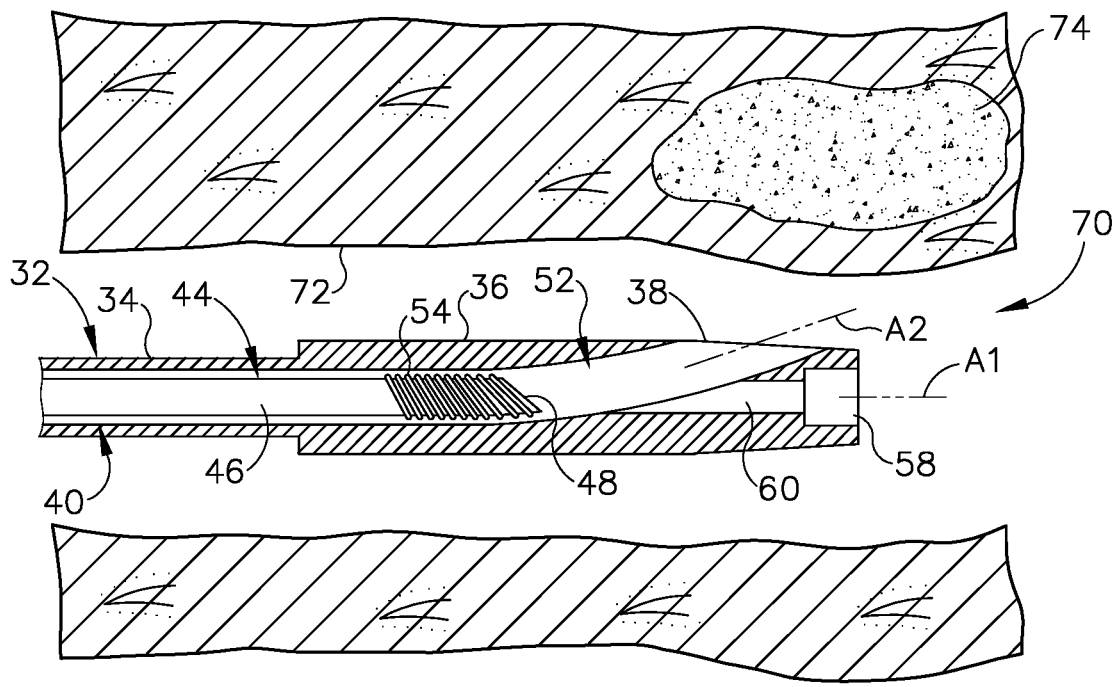
FIG. 4A depicts a schematic side cross-sectional view of a distal end portion of the sensor guided instrument of FIG. 3, showing the instrument arranged within an anatomical passageway.
Figure 4B:
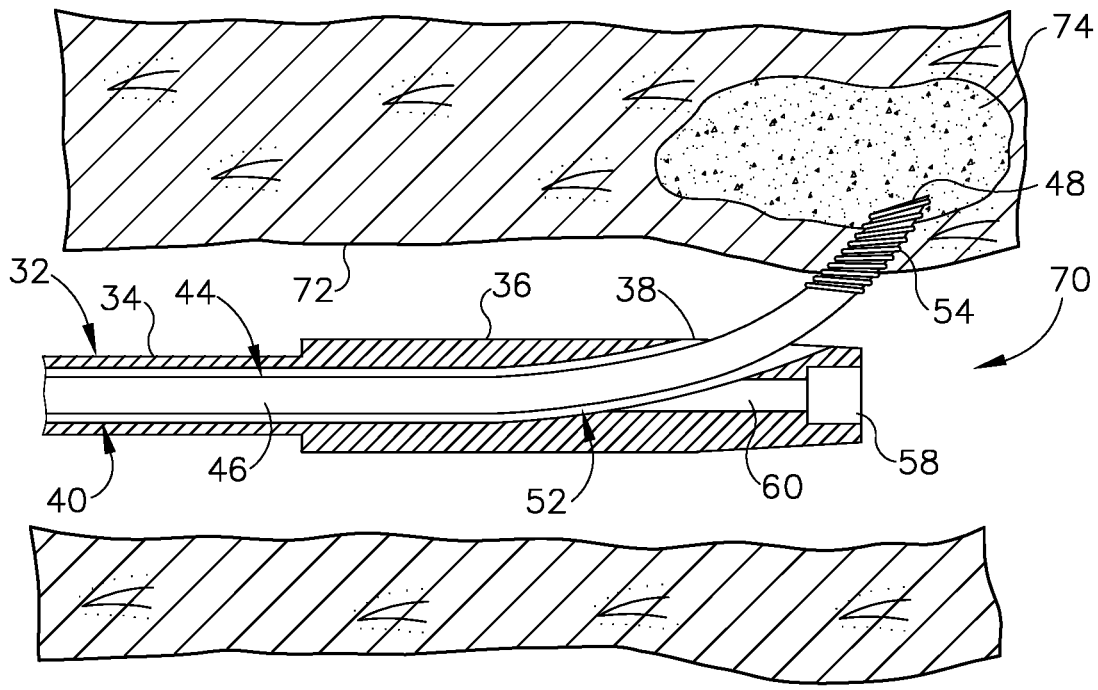
FIG. 4B depicts a schematic side cross-sectional view of the sensor guided instrument and anatomical passageway of FIG. 4A, showing a needle of the instrument in an extended position.

FIGS. 3-4B show additional details of sensor guided instrument (30) of IGS navigation system (10). Instrument (30) includes a catheter assembly (32) having an elongate catheter shaft (34) and a catheter tip (36) coupled to a distal end of catheter shaft (34). Catheter tip (36) may be releasably or permanently coupled to catheter shaft (34), and includes a needle port (38) that opens to a catheter lumen (40) through a side surface (42) of catheter tip (36). As described below, in other configurations needle port (38) may open to catheter lumen (40) through a distal end of catheter tip (36), such that needle port (38) is arranged coaxially with catheter lumen (40) along a linear path extending through catheter tip (36).

A needle (44) is slidably disposed within catheter lumen (40) and includes an elongate needle shaft (46), a sharpened needle tip (48) arranged at a distal end of needle shaft (46) and configured to penetrate tissue, and a needle lumen (50) having an open distal end at needle tip (48). As described in greater detail below, needle (44) is configured to aspirate a tissue biopsy sample proximally into needle lumen (50), as well as deliver a liquid therapeutic agent distally through needle lumen (50) to tissue. As shown in FIGS. 4A and 4B, needle (44) is configured to translate proximally and distally within catheter lumen (40). FIG. 4A shows an exemplary proximal needle position in which needle tip (48) is housed within catheter lumen (40). FIG. 4B shows an exemplary distal needle position in which needle tip (48) extends laterally through needle port (38).

As best seen in FIGS. 4A and 4B, a distal portion of catheter lumen (40) extends distally through catheter tip (36) to define a needle channel (52) that opens distally to needle port (38). In the present example, a proximal portion of needle channel (52) extends linearly along a primary axis (A1). A distal portion of needle channel (52) extends along a curved path toward needle port (38), so as to direct a protruding distal portion of needle (44) along a port axis (A2) when needle (44) is translated distally. Port axis (A2) is angularly offset from primary axis (A1) by any suitable degree so as to provide the curved distal portion of needle channel (52) with a suitable degree of curvature. In alternative configurations, the distal portion of needle channel (52) may be reconfigured to extend linearly from the linear proximal channel portion, to thereby direct needle tip (48) toward its extended position through a distal end of catheter tip (36) along primary axis (A1), rather than along angled port axis (A2).

Sensor guided instrument (30) further includes a tracking sensor in the form of an electromagnetic sensor coil (54). In the present example, sensor coil (54) is arranged on and wraps about an outer surface of a distal end portion of needle (44), such that a central axis of sensor coil (54) is aligned with a central axis of needle (44). A distal end of sensor coil (54) terminates at or immediately adjacent to needle tip (48). Sensor coil (54) is formed with a wire diameter that is sufficiently small to enable needle tip (48) to translate through needle port (38) and penetrate tissue (72) without snagging or generating undue friction against catheter tip (36) or tissue penetrated by needle (44).

Sensor coil (54) is formed of any suitable electrically conductive wire material, such as nitinol, for example. In the present example, needle (44) is also formed of any suitable electrically conductive material, such that needle and sensor coil (54) are electrically coupled together via direct contact with one another. A proximal portion of needle (44) is then electrically coupled with coupling unit (24). In other examples, sensor coil (54) may be electrically coupled with coupling unit (24) via a conductive wire (not shown), such as a twisted pair wire. As shown schematically in FIG. 3, sensor coil (54) is in communication with processor (16) by a communication path (56), thereby enabling processor (16) to receive electric signals emitted by sensor coil (54). In the present example, a distal portion of communication path (56) is provided by needle (44) via its direct electrical coupling with sensor coil (54). Alternatively, the distal portion of communication path (56) may be provided by a conductive wire, as described above. A proximal portion of communication path (56) may be provided by coupling unit (24) via its electrical coupling with needle (44). In such a configuration, coupling unit (24) is configured to communicate to processor (16) the signals received from sensor coil (54). In other configurations, sensor coil (54) or needle (44) may be directly, electrically coupled with processor (16), rather than through coupling unit (24), such as with a twisted pair wire.

In use, as shown in FIGS. 4A and 4B, catheter assembly (32) is inserted into an anatomical passageway (70) of a patient with needle (44) in the retracted position. Anatomical passageway (70) may be in the form of a paranasal sinus cavity, an ostium thereof, or an anatomical passageway of another portion of the patient body, such as a passageway within the lungs or trachea, for example. In the present example, anatomical passageway (70) is in the form of a paranasal sinus having a tissue wall (72) and a lesion (74) embedded within tissue wall (72). Instrument (30) is advanced distally through paranasal sinus (70) toward lesion (74) to perform a biopsy or treatment procedure on lesion (74) and/or tissue (72) surrounding lesion (74).

As instrument (30) is directed distally through paranasal sinus (70), sensor coil (54) moves with needle (44) relative to the electromagnetic field generated by field generators (12). This relative movement results in the generation of an electric current (or "signal") within sensor coil (54). This electric signal is communicated proximally to processor (16) through needle (44), or through a separate conductive wire as described above, along communication path (56). Processor (16) receives and analyzes the characteristics of this signal, and determines a location of sensor coil (54) within a three-dimensional space occupied by the electromagnetic field. In particular, processor (16) executes an algorithm to calculate three-dimensional location coordinates of sensor coil (54) from the location-related signals emitted by sensor coil (54). Because sensor coil (54) is coupled to needle (44) at its needle tip (48), the resulting location data indicates a precise location of needle tip (48) within the patient. Processor (16) then communicates with display screen (22), via console (18), to display the location of needle tip (48) relative to an image of the patient's head, or relative to a three-dimensional model of the anatomy within and adjacent to the patient's nasal cavity. This display provides the surgeon with a virtual rendering of needle tip (48) at its actual location within the patient in real time, thereby enabling the surgeon to ensure proper positioning of needle tip (48) relative to tissue (72) and lesion (74).

As described above, sensor guided instrument (30) may be deployed within paranasal sinus (70) to collect one or more biopsy samples of lesion (74), and/or to deliver a liquid substance such as a therapeutic drug or irrigation fluid to lesion (74) and/or surrounding tissue (72). With the assistance of the position tracking abilities provided by sensor coil (54) in combination with processor (16) and display screen (22), described above, a surgeon is able to track the precise location of needle tip (48) relative to paranasal sinus (70) and lesion (74). This enables the surgeon to position catheter assembly (32) appropriately such that needle (44) may be extended through needle port (38) and penetrate tissue wall (72) to thereby access lesion (74). Because sensor coil (54) extends fully distally to needle tip (48), the surgeon is able to precisely monitor the depth to which needle tip (48) has penetrated tissue (72) and/or lesion (74). This ability may be particularly advantageous when lesion (74) is arranged beneath the surface of tissue wall (72), such that needle tip (48) must penetrate tissue wall (72) by a specific depth in order to access lesion (74).

Upon positioning needle tip (48) in contact with lesion (74), the surgeon may aspirate a sample of lesion (74) into needle lumen (50) by applying a negative pressure (i.e., suction) to needle lumen (50). Alternatively, the surgeon may dispense a liquid substance contained within needle lumen (50), such as a therapeutic agent or an irrigation fluid, by applying a positive pressure to needle lumen (50). Pressures may be applied to needle lumen (50) for aspirating and dispensing using various mechanisms that will be readily apparent to those of ordinary skill in the art.

Figure 6:
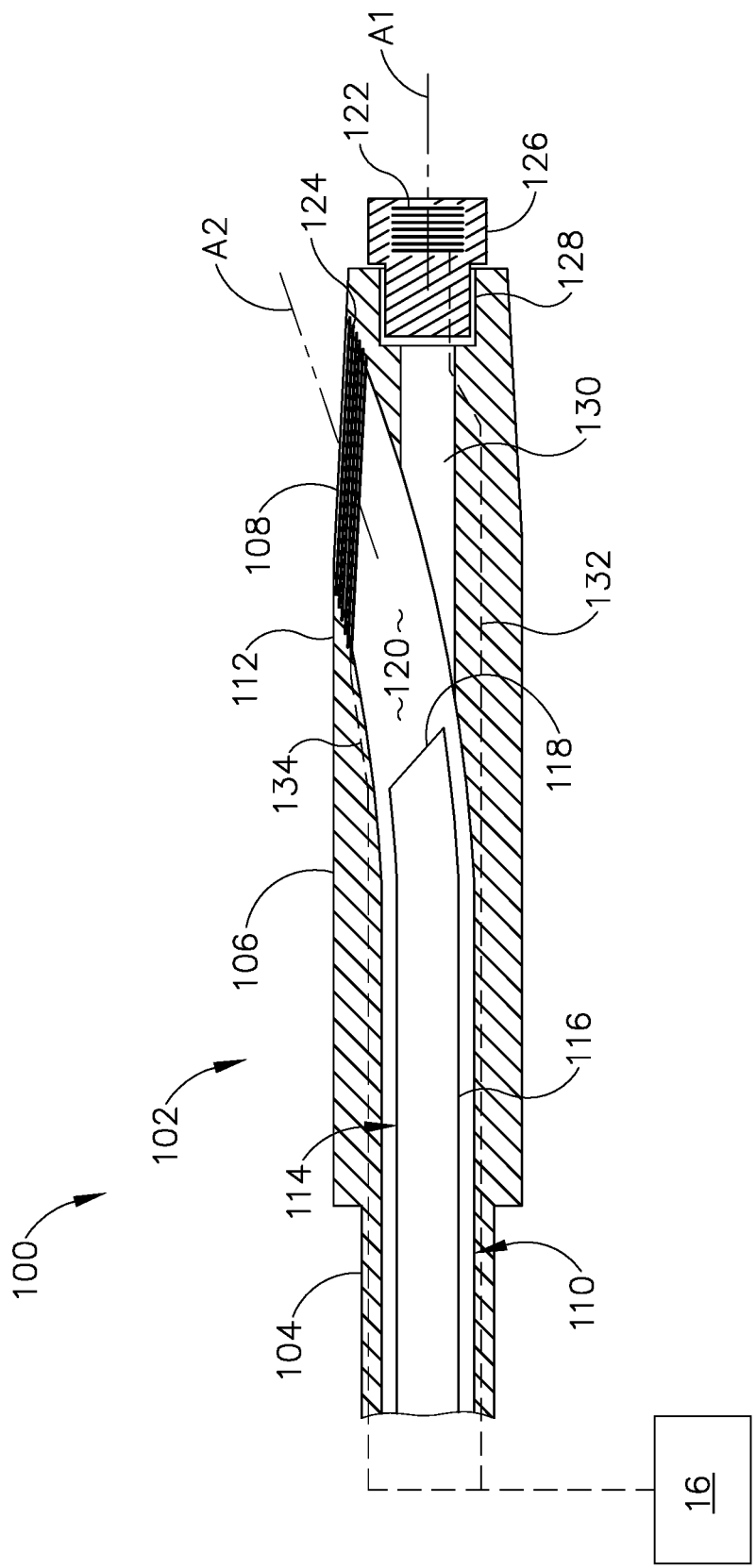
FIG. 6 depicts a schematic side sectional view of another exemplary sensor guided instrument configured for use with the sinus surgery navigation system of FIG. 1.

As shown in FIGS. 4A and 4B, catheter tip (36) of the present example further includes a distal opening (58) formed in a distal-most end of catheter tip (36), and an auxiliary channel (60) extending between distal opening (58) and needle channel (52) along primary axis (A1). Distal opening (58) may be configured to receive a secondary tracking sensor, such as a sensor structure (126) housing a sensor coil (122), as shown in FIG. 6. The secondary tracking sensor may be arranged in communication with processor (16) by a communication path similar to second communication path (134) described below. The secondary tracking sensor may communicate with processor (16) to provide signals relating to a location of catheter tip (36) within the patient, while sensor coil (54) communicates with processor (16) to provide signals relating a location of needle tip (48) within the patient. The signals provided by sensor coil (54) and the secondary tracking sensor may enable an operator to track a position of needle tip (48) relative to catheter tip (36), for example to precisely monitor the degree to which needle (44) has been extended from catheter tip (36).

C. Exemplary Alternative Needle Having Helical Recess

Figure 5:
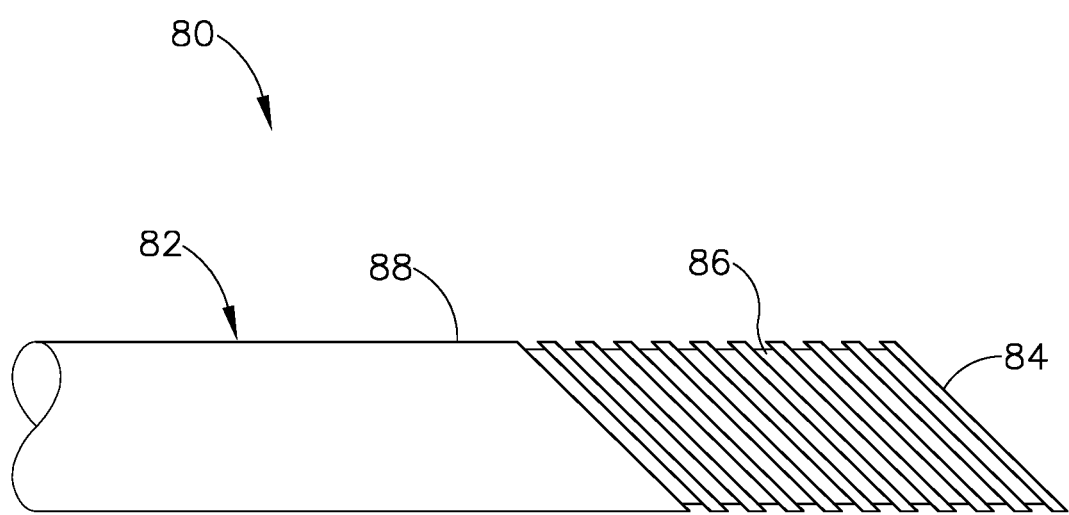
FIG. 5 depicts a side elevational view of another exemplary needle configured for use with the sensor guided instrument of FIG. 3.

FIG. 5 shows another exemplary needle (80) configured for use with sensor guided instrument (30). Needle (80) is similar to needle (44) described above in that needle (80) includes an elongate needle shaft (82), a sharpened needle tip (84) arranged at a distal end of needle shaft (82) and configured to penetrate tissue, and a needle lumen (not shown) having an open distal end at needle tip (84). Needle (80) further includes a recess (86) formed in an outer surface (88) of a distal end portion of needle shaft (82). In the present example, recess (86) is formed with a helical shape such that recess (86) is configured to receive sensor coil (54). Additionally, recess (86) is formed with a radial depth sufficient to enable sensor coil (54) to sit generally flush with outer surface (88), thereby minimizing friction and/or snagging otherwise caused by sensor coil (54) contacting an inner wall of catheter lumen (40) and/or patient anatomy during use. Additionally, a distal end of helical recess (86) is positioned immediately adjacent to distal needle tip (84), so as to position a distal end of sensor coil (54) immediately adjacent to needle tip (84). As described above, positioning sensor coil (54) immediately adjacent to needle tip (84) enables precise tracking of the position of needle tip (84) relative to patient anatomy. It will be appreciated that in other examples, recess (86) may be formed with various other shapes suitable for accommodating tracking sensors of various alternative configurations.

II. Exemplary Alternative Sensor Guided Instrument Having First and Second Sensor Coils on Catheter Tip FIG. 6 shows another exemplary sensor guided instrument (100) configured for use with IGS navigation system (10). Sensor guided instrument (100) is similar to sensor guided instrument (30) described above in that instrument (100) includes a catheter assembly (102) having an elongate catheter shaft (104) and a catheter tip (106) coupled to a distal end of catheter shaft (104). Catheter tip (106) includes a needle port (108) that opens to a catheter lumen (110) through a side surface (112) of catheter tip (106). Instrument (100) further includes a needle (114) slidably disposed within catheter lumen (110). Needle (114) has an elongate needle shaft (116), a sharpened needle tip (118) arranged at a distal end of needle shaft (116) and configured to penetrate tissue, and a needle lumen (not shown) having an open distal end at needle tip (118). A distal portion of catheter lumen (110) extends distally through catheter tip (106) to define a needle channel (120) that opens distally to needle port (108) and has a linear proximal channel portion and a curved distal channel portion. Linear proximal channel portion extends along a primary axis (A1) of catheter tip (106), and curved distal channel portion curves laterally toward and opens to needle port (108), and is configured to direct needle (114) along a port axis (A2) that is angularly offset from primary axis (A1).

Sensor guided instrument (100) further includes first and second tracking sensors in the form of first and second sensor coils (122, 124). First sensor coil (122) is arranged within a sensor structure (126) coupled to a distal end of catheter tip (106), and extends distally from catheter tip (106) along primary axis (A1). A proximal end of sensor structure (126) is received within a distal opening (128) of catheter tip (106), which opens to an auxiliary channel (130) that communicates with the curved distal portion of needle channel (120) along primary axis (A1). Second sensor coil (124) is arranged within catheter tip (106) and encircles curved distal portion of needle channel (120) adjacent to needle port (108), such that second sensor coil (124) is positioned about angled port axis (A2). Accordingly, first and second sensor coils (122, 124) are positioned about respective axes (A1, A2) that are angled relative to one another such that axes (A1, A2) are neither coaxial with nor parallel to one another. Furthermore, first and second sensor coils (122, 124) are axially spaced from one another such that no portions of either sensor coil (122, 124) overlap one another. Advantageously, this configuration enables precise tracking of a position and a rotational orientation of catheter tip (106), about the longitudinal axis of catheter shaft (104), relative to patient anatomy as catheter tip (106) moves through the surrounding electromagnetic field generated by field generators (12), as described in greater detail below. It will be appreciated that first and second sensor coils (122, 124) may be arranged in various other configurations in which sensor coils (122, 124) (i) are positioned about respective axes that are angled relative to one another, and (ii) do not overlap one another, so as to achieve the same position tracking benefits described above.

As shown schematically in FIG. 6, first sensor coil (122) is in communication with processor (16) by a first communication path (132), and second sensor coil (124) is in communication with processor (16) by a second communication path (134), such that processor (16) is configured to receive electric signals emitted by sensor coils (122, 124) along communication paths (132, 134). A distal portion of each communication path (132, 134) may comprise an electrical lead coupled to the respective sensor coil (122, 124) and extending proximally through opposing walls of catheter assembly (102). A proximal portion of each communication path (132, 134) may be provided by coupling unit (24) coupled to the electrical leads. In such a configuration, coupling unit (24) is configured to communicate to processor (16) the signals received from first and second sensor coils (122, 124). In other configurations, first and second sensor coils (122, 124) may be directly, electrically coupled with processor (16), rather than through coupling unit (24). Additionally, in other configurations, needle (114) may be provided with a third sensor coil similar to sensor coil (54) described above, which may electrically couple with needle (114) and communicate with processor (16) via a third communication path (not shown) extending proximally through needle (114), similar to communication path (56) described above.

As described above, first sensor coil (122) is arranged about primary axis (A1) at a distal-most end of catheter tip (106), and second sensor coil (124) is arranged about angled port axis (A2) at a location immediately adjacent to needle port (108). Accordingly, first sensor coil (122) is configured to generate and communicate to processor (16), via first communication path (132), electric signals corresponding to a location of the distal-most end of catheter tip (106) relative to patient anatomy, in response to movement of catheter tip (106) through the surrounding electromagnetic field. Simultaneously, second sensor coil (124) is configured to generate and communicate to processor (16), via second communication path (134), electric signals corresponding to a location of needle port (108), and thus of needle tip (118) when extended to needle port (108), relative to patient anatomy in response to movement of catheter tip (106) through the electromagnetic field.

Because second sensor coil (124) is located at needle port (108) and is radially offset from primary axis (A1), as shown in FIG. 6, the signals provided by second sensor coil (124) enable processor (16) to determine a rotational orientation of catheter tip (106) about primary axis (A1) relative to adjacent patient anatomy, such as tissue wall (72). When needle tip (118) is extended at least partially toward needle port (108) in a direction away from primary axis (A1), the rotational orientation of needle tip (118) relative to adjacent patient anatomy coincides with the rotational orientation of catheter tip (106) relative to the patient anatomy. Furthermore, the signals provided by second sensor coil (124) enable processor (16) to determine a distance between needle port (108) and adjacent anatomy along port axis (A2). Processor (16) may reference this distance in combination with a known distance by which needle (114) has been extended in order to determine a location of needle tip (118) relative to the patient anatomy, and thus a tissue penetration depth of needle tip (118), and thereby provide corresponding feedback to the operator. Alternatively, needle (114) may be provided with its own sensor coil, similar to sensor coil (54) described above, to track the precise location and tissue penetration depth of needle tip (118).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a catheter configured to be inserted into an anatomical passageway of a patient, wherein the catheter includes a catheter lumen; (b) a distal segment having a port, wherein the port communicates with the catheter lumen; (c) a needle slidably disposed within the catheter lumen, wherein the needle is translatable relative to the catheter between a retracted position and an extended position, wherein a needle distal end is configured to extend through the port when the needle is in the extended position; and (d) a tracking sensor coupled to the needle, wherein the tracking sensor is configured to generate a signal corresponding to a location of the needle distal end within the patient.

Example 2

The surgical instrument of Example 1, wherein the tracking sensor is arranged on the needle distal end.

Example 3

The surgical instrument of any one or more of the preceding Examples, wherein the tracking sensor comprises an electromagnetic sensor configured to generate an electric signal in response to movement of the electromagnetic sensor through an electromagnetic field.

Example 4

The surgical instrument of Example 3, wherein the electromagnetic sensor comprises a coil.

Example 5

The surgical instrument of Example 4, wherein the coil defines a coil axis that remains in coaxial alignment with a longitudinal axis of the needle while the needle translates between the retracted position and the extended position.

Example 6

The surgical instrument of any one or more of Examples 1 through 5, wherein a distal end of the tracking sensor extends to a distal tip of the needle distal end

Example 7

The surgical instrument of any one or more of Examples 1 through 6, wherein the tracking sensor is provided on an outer surface of the needle.

Example 8

The surgical instrument of any one or more of Examples 1 through 6, wherein the needle distal end includes a recess, wherein the tracking sensor is arranged in the recess.

Example 9

The surgical instrument of Example 8, wherein the recess comprises a helical recess, wherein the tracking sensor comprises a sensor coil arranged in the helical recess.

Example 10

The surgical instrument of any one or more of Examples 1 through 9, wherein the distal segment includes a needle channel extending therethrough along a non-linear path, wherein the port communicates with the catheter lumen via the needle channel.

Example 11

The surgical instrument of any one or more of Examples 1 through 10, wherein the port is arranged in a side portion of the distal segment, wherein the port defines a port axis that is angularly offset from a longitudinal axis of the distal segment.

Example 12

The surgical instrument of any one or more of Examples 1 through 11, wherein the needle includes a needle lumen, wherein the needle is operable to at least one of: (i) aspirate a tissue sample into the needle lumen, or (ii) deliver a liquid substance to tissue.

Example 13

A surgical system comprising: (a) the surgical instrument of any or more of Examples 1 through 12, wherein the tracking sensor is configured to generate a signal in response to movement of the needle distal end within the patient; and (b) a processor, wherein the processor is configured to receive the signal and determine a location of the needle distal end within the patient based on the signal.

Example 14

The surgical system of Example 13, further comprising at least one field generating element configured to generate an electromagnetic field around the portion of the patient containing the anatomical passageway through which the catheter is inserted.

Example 15

The surgical system of Example 14, wherein the tracking sensor comprises a coil configured to generate an electric signal in response to movement of the coil through the electromagnetic field.

Example 16

A surgical instrument comprising: (a) a catheter configured to be inserted into an anatomical passageway of a patient, wherein the catheter includes a catheter lumen; (b) a distal segment having a port, wherein the port communicates with the catheter lumen; (c) a needle slidably disposed within the catheter lumen, wherein the needle is translatable relative to the catheter between a retracted position and an extended position, wherein a needle distal end is configured to extend through the port and penetrate tissue when the needle is in the extended position; and (d) at least one tracking sensor, wherein the at least one tracking sensor is configured to communicate with a processor for determining at least one of: (i) a tissue depth to which the needle distal end has penetrated the tissue, or (ii) a rotational orientation of the distal segment relative to the tissue.

Example 17

The surgical instrument of Example 16, wherein the at least one tracking sensor comprises a tracking sensor coupled to the needle.

Example 18

The surgical instrument of any one or more of Examples 16 through 17, wherein the at least one tracking sensor comprises a plurality of tracking sensors coupled to the distal segment.

Example 19

A surgical instrument comprising: (a) a catheter configured to be inserted into an anatomical passageway of a patient, wherein the catheter includes a catheter lumen; (b) a distal segment extending longitudinally along a first axis, wherein the distal segment includes a port that communicates with the catheter lumen; (c) a needle slidably disposed within the catheter lumen, wherein the needle is translatable relative to the catheter between a retracted position and an extended position, wherein a needle distal end is configured to extend through the port and toward tissue when the needle is in the extended position; and (d) a tracking sensor configured to generate a signal in response to movement of the tracking sensor through an electromagnetic field, wherein the tracking sensor is configured to extend along a second axis when the needle is in the extended position, wherein the second axis is angularly offset from the first axis.

Example 20

The surgical instrument of Example 19, wherein the tracking sensor comprises an electromagnetic sensor.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a catheter configured to be inserted into an anatomical passageway of a patient, wherein the catheter includes a catheter lumen;
   (b) a distal segment having a port, wherein the port communicates with the catheter lumen;
   (c) a needle slidably disposed within the catheter lumen, wherein the needle is translatable relative to the catheter between a retracted position and an extended position, wherein a needle distal end is configured to extend through the port when the needle is in the extended position, wherein the needle distal end includes a recess, wherein the recess extends circumferentially around a longitudinal axis of the needle; and
   (d) a tracking sensor arranged within the recess of the needle, wherein the tracking sensor extends circumferentially about an exterior surface of the needle at the needle distal end, wherein the tracking sensor is configured to generate a signal corresponding to a location of the needle distal end within the patient.

2. The surgical instrument of claim 1, wherein the tracking sensor is arranged on the needle distal end.

3. The surgical instrument of claim 1, wherein the tracking sensor is provided on an outer surface of the needle.

4. The surgical instrument of claim 1, wherein the recess comprises a helical recess, wherein the tracking sensor comprises a sensor coil arranged in the helical recess.

5. The surgical instrument of claim 1, wherein the distal segment includes a needle channel extending therethrough along a non-linear path, wherein the port communicates with the catheter lumen via the needle channel.

6. The surgical instrument of claim 1, wherein the port is arranged in a side portion of the distal segment, wherein the port defines a port axis that is angularly offset from a longitudinal axis of the distal segment.

7. The surgical instrument of claim 1, wherein the needle includes a needle lumen, wherein the needle is operable to at least one of:
   (i) aspirate a tissue sample into the needle lumen, or
   (ii) deliver a liquid substance to tissue.

8. The surgical instrument of claim 1, further comprising a secondary tracking sensor coupled to a distal end of the catheter, wherein the secondary tracking sensor is configured to generate a secondary signal corresponding to the location of the needle distal end within the patient.

9. The surgical instrument of claim 1, wherein the tracking sensor comprises an electromagnetic sensor configured to generate an electric signal in response to movement of the electromagnetic sensor through an electromagnetic field.

10. The surgical instrument of claim 9, wherein the electromagnetic sensor comprises a coil.

11. The surgical instrument of claim 10, wherein the coil defines a coil axis that remains in coaxial alignment with a longitudinal axis of the needle while the needle translates between the retracted position and the extended position.

12. A surgical system comprising:
   (a) the surgical instrument of claim 1, wherein the tracking sensor is configured to generate a signal in response to movement of the needle distal end within the patient; and
   (b) a processor, wherein the processor is configured to receive the signal and determine a location of the needle distal end within the patient based on the signal.

13. The surgical system of claim 12, further comprising at least one field generating element configured to generate an electromagnetic field around a portion of the patient containing the anatomical passageway through which the catheter is inserted.

14. A surgical instrument comprising:
   (a) a catheter configured to be inserted into an anatomical passageway of a patient, wherein the catheter includes a catheter lumen, wherein a distal end of the catheter includes a port, wherein the port communicates with the catheter lumen;
   (b) a needle slidably disposed within the catheter lumen, wherein the needle includes a first portion defining a first outer surface diameter, wherein a needle distal end defines a second portion having a recess formed on an outer surface of the needle and extending circumferentially around a longitudinal axis of the needle distal end, wherein the recess includes a base surface which defines a second outer surface diameter that is less than the first outer surface diameter, wherein the needle is translatable relative to the catheter between a retracted position and an extended position, wherein the needle distal end is configured to extend through the port when the needle is in the extended position; and (c) a tracking sensor coupled to the needle, wherein the tracking sensor is arranged within the recess, wherein the tracking sensor is configured to generate a signal corresponding to a location of the needle distal end within the patient.

15. The surgical instrument of claim 14, wherein the tracking sensor comprises an electromagnetic sensor configured to generate an electric signal in response to movement of the electromagnetic sensor through an electromagnetic field.

16. The surgical instrument of claim 15, wherein the electromagnetic sensor comprises a coil.

17. The surgical instrument of claim 16, wherein the coil is configured to be flush with the first outer surface diameter of the first portion of the needle.

18. A surgical instrument comprising:

(a) a catheter configured to be inserted into an anatomical passageway of a patient, wherein the catheter includes a catheter lumen;

(b) a needle slidably disposed within the catheter lumen, wherein the needle is translatable relative to the catheter between a retracted position and an extended position, wherein the needle distal end is configured to extend outward from the catheter when the needle is in the extended position, wherein the needle distal end is configured to pierce a tissue, wherein the needle distal end includes a recess that extends circumferentially around an exterior surface of the needle distal end; and (c) a tracking sensor coupled with an exterior surface of the needle, wherein the tracking sensor is positioned in the recess, wherein the tracking sensor is configured to be flush with the exterior surface of the needle, wherein the tracking sensor is configured to generate a signal corresponding to a location of the needle distal end within the patient.

19. The surgical instrument of claim 18, wherein the tracking sensor wraps circumferentially around the exterior surface of the needle distal end.

20. The surgical instrument of claim 18, wherein the tracking sensor comprises a coil configured to generate an electric signal in response to movement of the coil through an electromagnetic field.

* * * * *